(12) United States Patent
Mosavi

(10) Patent No.: US 9,452,494 B2
(45) Date of Patent: Sep. 27, 2016

(54) LASER SYSTEMS FOR DRILLING HOLES IN MEDICAL DEVICES

(71) Applicant: Ethicon, Inc., Somerville, NJ (US)

(72) Inventor: Reza K. Mosavi, Alto, GA (US)

(73) Assignee: Ethicon, Inc., Somerville, NJ (US)

( * ) Notice: Subject to any disclaimer, the term of this patent is extended or adjusted under 35 U.S.C. 154(b) by 260 days.

(21) Appl. No.: 13/800,014

(22) Filed: Mar. 13, 2013

(65) Prior Publication Data

US 2014/0263215 A1 Sep. 18, 2014

(51) Int. Cl.
| | |
|---|---|
| B23K 26/38 | (2014.01) |
| B21G 1/08 | (2006.01) |
| A61B 17/00 | (2006.01) |
| A61B 17/06 | (2006.01) |

(52) U.S. Cl.
CPC ............... *B23K 26/385* (2013.01); *B21G 1/08* (2013.01); *B23K 26/386* (2013.01); *A61B 2017/00526* (2013.01); *A61B 2017/061* (2013.01)

(58) Field of Classification Search
CPC .. B23K 26/365; B23K 26/38; B23K 26/381; B23K 26/383; B23K 26/385; B23K 26/386
See application file for complete search history.

(56) References Cited

U.S. PATENT DOCUMENTS

| | | |
|---|---|---|
| 5,630,268 A | 5/1997 | Smith |
| 5,644,834 A | 7/1997 | Smith |
| 5,661,893 A | 9/1997 | Smith |
| 5,701,656 A | 12/1997 | Smith |
| 5,776,268 A | 7/1998 | McJames |
| 5,913,875 A | 6/1999 | Smith |
| 6,018,860 A | 2/2000 | Smith |
| 6,252,195 B1* | 6/2001 | Mosavi et al. ........... 219/121.69 |
| 6,347,007 B1 | 2/2002 | Grubb |
| 6,683,276 B2 | 1/2004 | Mosavi |
| 7,394,591 B2 | 7/2008 | Harter |
| 7,535,628 B2 | 5/2009 | Tsuchiya |
| 7,688,499 B2 | 3/2010 | Fermann |
| 7,715,459 B2 | 5/2010 | Brown |
| 7,720,121 B2 | 5/2010 | Peng |
| 7,724,787 B2 | 5/2010 | Murison |
| 7,813,394 B2 | 10/2010 | Peng |
| 7,929,203 B2 | 4/2011 | Harter |
| 8,031,396 B2 | 10/2011 | Fermann |
| 8,165,178 B2 | 4/2012 | Henderson |
| 2004/0134894 A1 | 7/2004 | Gu et al. |
| 2009/0097515 A1* | 4/2009 | Harter ................... H01S 3/0092 372/25 |
| 2010/0054284 A1* | 3/2010 | Dekker ................. H01S 3/1086 372/3 |
| 2011/0085149 A1 | 4/2011 | Nathan |

FOREIGN PATENT DOCUMENTS

WO      WO2011123205 A1     10/2011

OTHER PUBLICATIONS

S.T.Hendow et al., "Percussion Drilling of Metals Using Bursts of Nanosecond Pulses", Optics Express, 2011, vol. 19, No. 11, pp. 10221-10231.
S.T.Hendow et al., "Mopa Pulsed Fiber Laser With Controlled Peak Power and Pulse Energy for Micromachining of Hard Materials", Paper M209, ICALEO 2009, Orlando Florida.

* cited by examiner

*Primary Examiner* — Brian Jennison
(74) *Attorney, Agent, or Firm* — E. Richard Skula

(57) ABSTRACT

Novel laser drilling systems are disclosed. The laser drilling systems are useful for drilling bore holes in medical devices, especially blind bore holes in surgical needles. The laser systems use a low power fiber seed laser to produce a high quality laser beam that is modulated and amplified, and which has precise characteristics to produce precision drilled holes.

10 Claims, 7 Drawing Sheets

LASER SYSTEMS FOR DRILLING HOLES IN MEDICAL DEVICES

FIELD OF THE INVENTION

The field of art to which this invention pertains is laser drilling systems, more particularly laser drilling systems for medical devices.

BACKGROUND OF THE INVENTION

Laser drilling systems for drilling holes in medical devices are known in the art. The laser drilling systems are often used to drill blind holes in the proximal ends of surgical needles. Conventional surgical needles typically have a suture mounting end to which a surgical suture is mounted. The proximal end may have a channel or a blind bore hole to receive the distal end of a surgical suture, which is then affixed to the needle mounting section using conventional techniques such as mechanical swaging, gluing, adhesives, etc. There is a preference for using needles having drilled blind bore holes versus channels. The needles having drilled bore holes tend to have a more regular profile after suture attachment when compared with surgical needles having a channeled mounting end. It is also possible to more closely match up the needle diameter with the diameter of the attached suture. This provides the advantage of having better perceived movement through tissue and less tissue drag, and a more narrow tissue pathway, potentially providing a superior clinical outcome such as improved hemostasis. On the other hand, channeled suture needles are more economical to produce.

A blind bore hole is typically drilled into the proximal end of a surgical needle using conventional methods including mechanical drilling and laser drilling. Although mechanical drilling may provide for a precisely drilled bore hole having a uniform configuration, it is known that mechanical drilling may have deficiencies associated with its use. Mechanical drilling requires drills that have a fine diameter in order to drill surgical needles having fine needle sizes, such as sizes 0.15 mm (0.006 in). Such drills are difficult to manufacture in fine diameter sizes and tend to wear out relatively quickly in a high speed production process. In addition, because of the fine wire sizes of the needles, and the fine diameters of the needle, the precision mechanical drilling equipment may require frequent downtime in order to precisely adjust and align the drills. Laser drilling systems overcome these deficiencies by providing high speed drilling capabilities without the need for expensive drills. In addition, there is minimal downtime for adjustments once the system has been set up. Another advantage of laser drilling systems is the ability to easily switch between the drilling of various needle wire diameters having different bore hole diameters and lengths.

Nd-YAG laser systems useful for drilling blind boreholes in surgical needles are disclosed in U.S. Pat. No. 6,252,195 and U.S. Pat. No. 6,683,276, both of which are incorporated by reference. These patents disclose diode pumped Nd-YAG laser drilling systems for surgical needles. The oscillator in these systems is diode pumped, and the amplifiers are diode pumped as well. High speed surgical needle manufacturing processes are described in U.S. Pat. Nos. 5,630,268, 5,644,834, 5,661,893, 5,701,656, 5,776,268, 5,913,875, 6,018,860, and 6,252,195, which are incorporated by reference. Such manufacturing processes, which process a surgical needle from a spool of wire to a surgical needle blank to a finished surgical needle, typically mount the needle blanks to a carrier strip, wherein in the strip and needle blanks are moved through progressive forming and processing stations to produce a finished surgical needle.

However, there are certain disadvantages associated with the laser drilling of surgical needles using conventional laser systems. In order to drill a bore hole of the desired diameter and depth in a structure such as the proximal end of a surgical needle, it is necessary to have a beam of sufficient power and quality. In addition, the laser drilling process is a percussive drilling process wherein a laser beam is chopped into a series of pulses. Percussive drilling is necessary since the drilling process produces molten and vaporized metal that is ejected out of the bore hole during the process. Accordingly, blind bore holes that are laser drilled typically tend to not have a perfectly symmetrical configuration. This can be an issue in suture attachment, especially with high speed automated systems. The geometry of the drilled bore hole may vary over time requiring frequent and precise quality assurance inspections, and associated laser and production downtime to adjust the laser system to bring the drilled bore holes into conformance with manufacturing specifications. In addition, variations in the laser beam parameters may result in deficiencies such as recast. Recast may affect the ability of the proximal end of a surgical needle having a laser-drilled borehole to be mechanically swaged in order to attach an end of a surgical suture without cracking the metal about the bore hole. Another deficiency that may be associated with conventional laser drilling systems for surgical needles is the inability to readily and easily drill a variety of different sizes of surgical needles. Currently available systems are typically set up to drill a narrow range of hole diameters, e.g., small boreholes, medium or large. Also, it is known that in order to drill acceptable bore holes in medium and larger diameter needles, it is typically necessary to apply an ink coating to the proximal end of the needle. This ink coating allows for more effective energy absorption and beam coupling. Typically, it is very difficult and impractical to drill the medium to large diameter needle sizes without this inking operation, which adds a level of complexity and increased costs to the manufacturing process.

There is a need in this art for novel laser drilling systems that provide superior performance with minimal downtime for adjustments. There is also a need for novel laser drilling systems for surgical needles that have high quality beams which provide high quality laser-drilled bore holes for suture mounting. In addition, there is a need for novel laser drilling systems for surgical needles that can precisely drill a variety needle wire sizes and that can be readily and easily adjusted to switch between wire sizes.

SUMMARY OF THE INVENTION

Novel laser drilling systems for drilling blind bore holes in medical devices such as surgical needles are disclosed. The laser systems have a low power fiber Nd-YAG seed laser that produces a high quality beam. The beam from the seed laser is directed to an electro-optical modulator where the beam is modulated or pulsed. The pulsed beam is then directed to at least one amplifier to amplify the beam to a sufficient strength for drilling a bore hole in a medical device. The beam is then directed to focusing optics for focusing the beam such that it can be directed to drill a desired blind bore in a medical device.

Another aspect of the present invention is a method of drilling bore holes in a medical device using the laser drilling system of the present invention.

These and other aspects and advantages of the present invention will become more apparent from the following description and accompanying drawings.

DETAILED DESCRIPTION OF THE INVENTION

Figure 1:
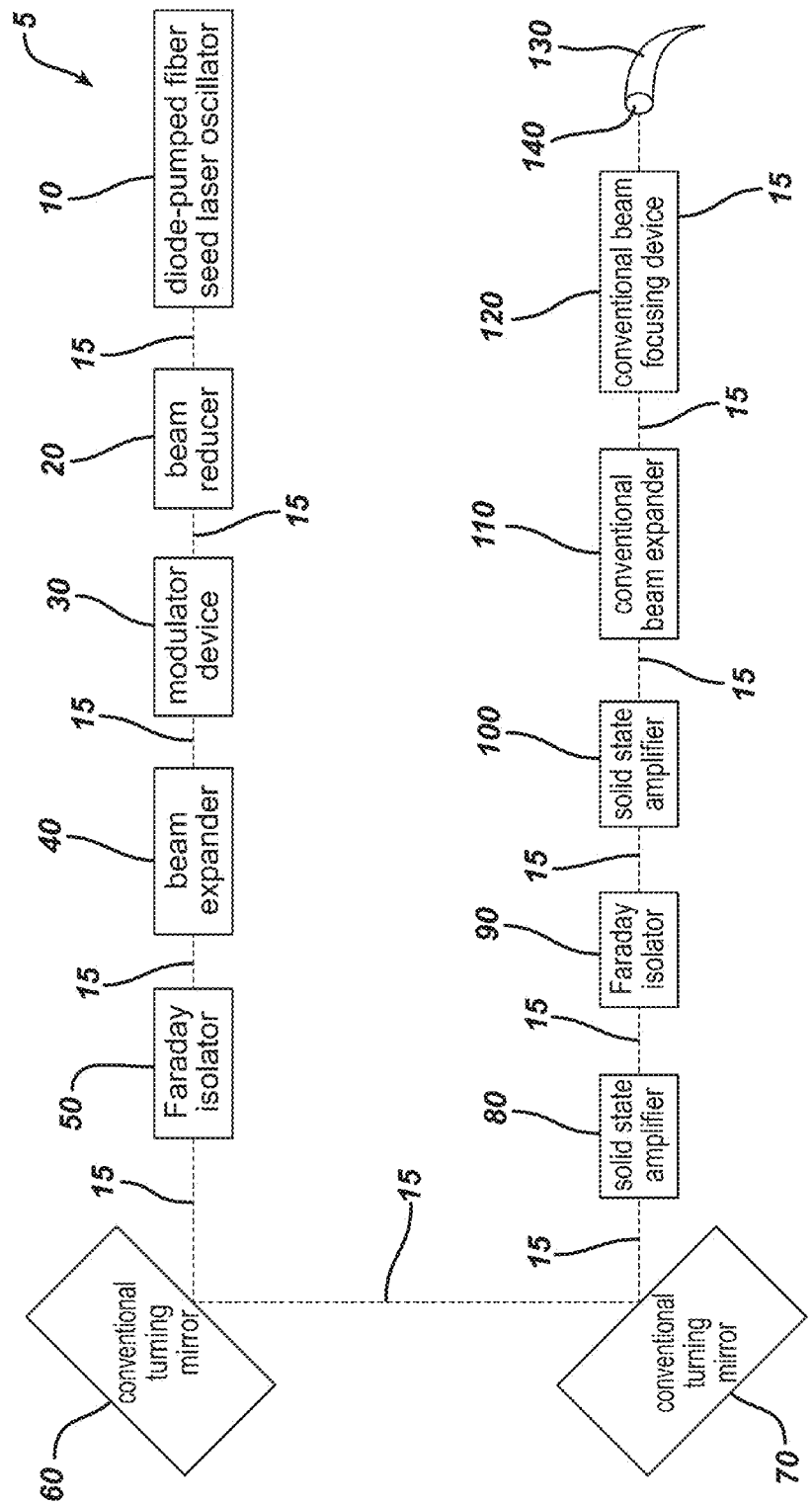
FIG. 1 is a schematic of a laser drilling system of the present invention.

The novel laser systems of the present invention utilize a seed laser to produce a high quality beam that is modulated and amplified to produce a high quality, pulsed, high power laser beam useful for precision percussive drilling. In particular, the laser drilling systems of the present invention are useful in drilling high quality blind bore holes in medical devices such as surgical needles. A schematic of a novel laser drilling system 5 of the present invention is seen in FIG. 1. A diode-pumped fiber seed laser oscillator 10 is seen to produce and direct a low power, high quality laser beam 15 to beam reducer 20. The beam reducer 20 is a conventional device that acts upon beam 15 to reduce the diameter of the beam. The reduced diameter beam 15 after exiting beam reducer 20 is directed to modulator device 30. Modulator device 30 is a conventional elecro-optical device (Pockels Cell) that modulates beam 15 into a wave train of equal pulses as required for drilling a bore hole in a percussive manner. Pulsed laser beam 15 then is directed to a beam expander 40. The beam expander 40 is a conventional device that acts upon beam 15 to increase the diameter of the beam. Pulsed laser beam 15 then is directed to Faraday isolator 50. Faraday isolator 50 is a conventional device that operates on the beam 15 by allowing beam to propagate in a forward direction only. After exiting Faraday isolator 50, the beam 15 is directed to conventional turning mirror 60, which directs the beam 15 to conventional turning mirror 70. The beam 15 is then directed by turning mirror 70 to first solid state amplifier 80. The solid state amplifier 80 is a conventional amplifier that is preferably flash lamp pumped, but may also be diode pumped if desired. Amplifier 80 acts upon the laser beam 15 by increasing the energy of the beam 15. After exiting the amplifier 80, the beam 15 is directed to Faraday isolator 90, which functions in a similar manner to Faraday isolator 50. The beam 15 is then directed to solid state amplifier 100, wherein the beam 15 is again amplified to a higher energy level. Amplifier 100 is similarly and preferably a conventional flash lamp pumped amplifier, but may also be diode pumped if desired. After exiting the amplifier 100, the beam 15 is then directed to conventional beam expander 110 where it is expanded. The beam 15 is then directed to conventional beam focusing device 120, which focuses the beam to the desired diameter. At this point the beam has the desired, sufficiently effective beam characteristics of power density, pulse width, pulse frequency, number of pulses, pulse shape and pulse peak power. The beam 15 is now directed to a point on a medical device for drilling a blind bore hole. Preferably, the medical device is a surgical needle, and the focused beam 15 is directed at the proximal end of the surgical needle 130 to drill a blind bore hole 140 having the desired characteristics of diameter, depth and dimensional uniformity. Although not shown in the schematic, the system may be controlled by a conventional computer that would adjust the pulse width, power density pulse frequency, number of pulses, pulse shape and pulse peak power and diameter of the laser beam by controlling the individual components based upon settings inputed by the operator. If desired, although not preferred, the novel systems of the present invention may be used to drill other types of bore holes in addition to blind bore holes, e.g., a through hole.

The seed lasers that can be used with the laser drilling systems of the present invention are conventional Nd-YAG seed laser oscillators that are commercially available. Such lasers are typically used in instrumentation for the following purposes: coherent beam combing, detection systems, sensing, and laboratory applications. The lasers will have the following characteristics: single frequency, linearly polarized, and beam quality ($M^2<1.4$). An example of a seed laser useful in the laser drilling system of the present invention is the YLR-50-1064-LP-SF fiber laser from IPG Photonics, Oxford, Mass. 01540, the manufacturer. This is a 50 W Yb Fiber Laser, linearly polarized, center wavelength 1064 nm, single frequency linewidth 70 kHz with beam quality $M^2=1.25$. The seed lasers will have a power output of about 10-50 watts, a pulse width of about 1-3 milliseconds and a frequency of about 2-3 Hz. The laser beam modulators useful in the laser drilling systems of the present invention include conventional, commercially available modulators having the following characteristics: having a Lithium Tantalate crystal. A conventional modulator useful in the practice of the present invention is the ConOptics (Danbury, Conn.) Model 360-80-02-DRY LTA 2.7 mm Dry Cell. The beam expanders useful in the laser systems of the present invention include conventional, commercially available laser beam expanders such as MegaWatt Lasers Inc. (Hilton Head, S.C.) beam expander. The beam expanders will have the following characteristics: adjustable expansion up to 6×. The Faraday isolators useful in the practice of the present invention include conventional, commercially available Faraday isolators such as the following: Electro-Optics Technology, Inc. (Traverse City, Mich.) Model 8I1055-WP2. The Faraday isolators will have, for example, the following characteristics: high power, 8 mm diameter, wavelength 1064 nm, polarization orientation of 90 degrees-90 degrees. The turning mirrors useful in the practice of the present invention will be conventional laser turning mirrors useful in laser systems including those available from Edmund Optics (Barrington, N.J.). The mirrors will have the following characteristics: 100% reflective for 1064 nm wavelength. The above description refers to a laser with a wavelength of 1064 nm, however other wavelengths are possible.

The amplifiers useful in the laser drilling systems of the present invention include conventional, commercially available amplifiers with Nd-YAG rods that are either flash lamp pumped or diode pumped. The amplifiers will preferably be flash lamp pumped if cost issues are an issue, and are also preferable due to easy availability. The amplifiers will have the following characteristics: Nd-YAG rod with anti-reflective coatings (AR) on both ends of the rod, for example AR at the wavelength of the laser, such as 1064 nm. An example of a preferred rod is 6.35 mm diameter rod. The amplifiers will typically have a voltage range 0 about 350-750 volts, a pulse width of about 200-700 microseconds, and a frequency of about 2-3 Hz. Amplifiers that are useful and are commercially available include the following: 6.35×150 FS pump chamber from MegaWatt Lasers, Inc., Hilton Head Island, S.C. The beam focusing lenses useful in the systems of the present invention include commercially available conventional focusing lens systems available from the following sources: LASAG (now Rofin-Sinar, Plymouth, Minn. 48170) model number 24.0105 or similar. The beam focusing lenses will have the following characteristics: lens doublet with 30 mm lens protection.

The laser beams produced by the laser drilling systems of the present invention will be sufficiently effective to drill bore holes in surgical needles having good dimensional conformity. The laser beams will have sufficient power, pulse frequency and pulse width to effectively drill blind holes, and other bore holes, in medical devices such as surgical needles. The laser beams will typically have a focused diameter of about 0.05 mm to about 0.45 mm, more typically about 0.1 mm to about 0.4 mm, and preferably about 0.2 mm to about 0.35 mm. The laser beams will have a pulse frequency of typically about 25 kHz to about 1000 kHz, more typically about 50 kHz to about 200 kHz, and preferably about 71 kHz to about 125 kHz. The peak power of the beam will typically be about 5 kW to about 80 kW, more typically about 10 kW to about 70 kW and preferably about 20 kW to about 60 kW. The average power of beam will be about 0.5 to about 80 Watts. The following are definitions of the Average Power and Peak Power:

1. Average Power=Laser energy×laser frequency: and, 2. Peak Power=Laser energy per pulse/pulse duration. For example with respect to average power, if the laser energy is 8 Joules and the laser fires at 3 shots per second then the Average Power is 8×3=24 Watts. Also for example regarding peak power, if the energy per pulse is 0.8 Joules and the pulse duration is 10 microseconds, then the Peak Power is $0.8/10^{-5}$=80 KW. The pulse width of the beam will typically be about 0.1 ms to about 2 ms, more typically about 0.5 ms to about 2 ms and preferably about 1 ms to about 1.5 ms. The frequency of the beam will typically be about 1 Hz to about 10 Hz, more typically about 2 Hz to about 10 Hz and preferably about 6 Hz to about 10 Hz.

The laser systems of the present invention will produce high quality, pulsed laser beams having the following characteristics. The pulses will typically be about 5 to 30 pulses, more typically about 6 to about 20 pulses, and preferably about 7 to about 15 pulses. The pulse duration will be typically be about 3 to 30 microseconds, more typically about 5 to about 15 microseconds, and preferably about 10 to about 12 microseconds depending on the hole size and material. The energy per pulse will typically be about 0.05 to 0.8 Joule, more typically about 0.1 to about 0.7 Joules and preferably about 0.2 to about 0.6 Joule depending on the hole size and material.

Figure 6:
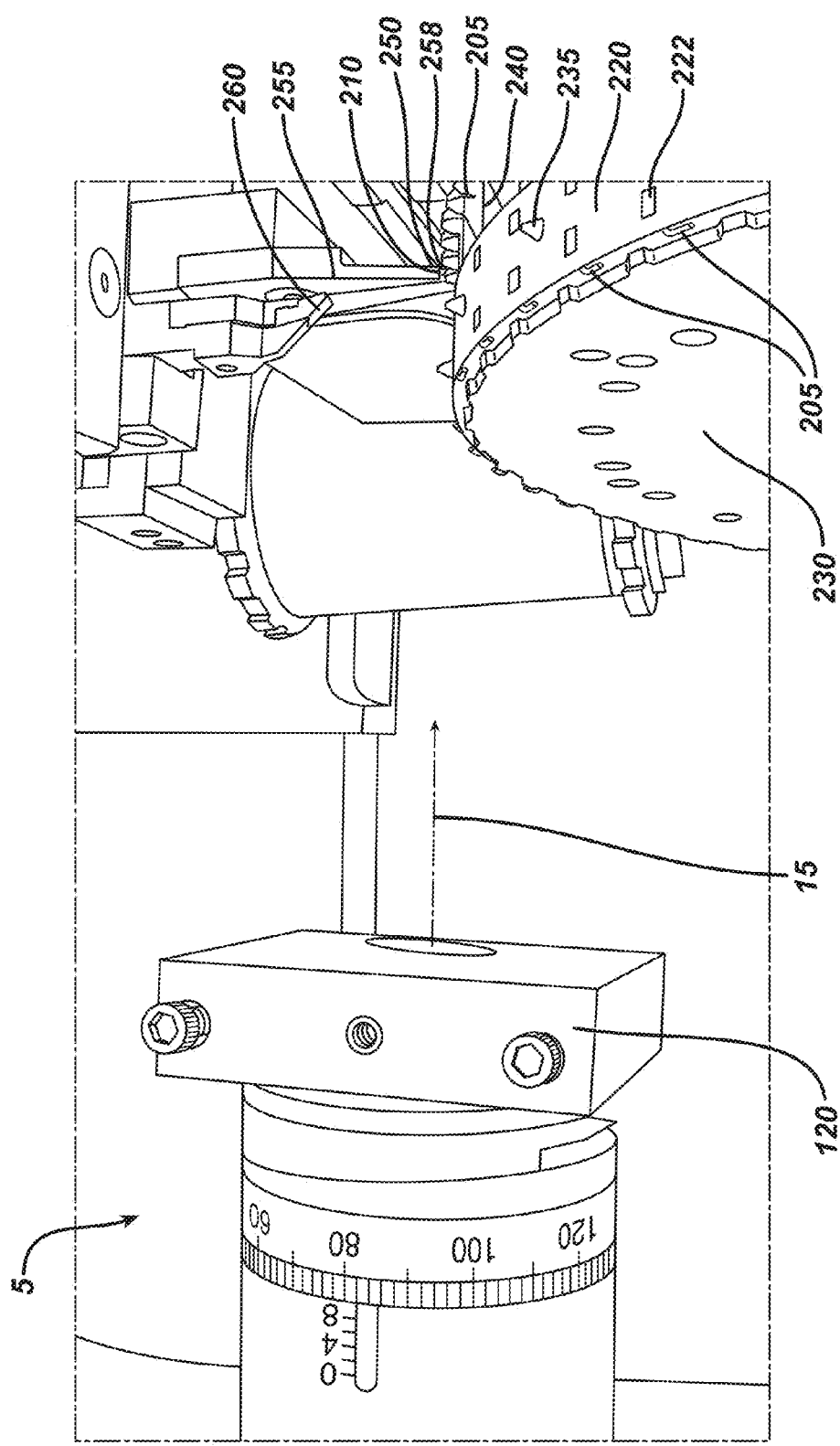
FIG. 6 is a perspective view of the end of a laser drilling system illustrating the focusing optics and a fixture that needles are held in while being drilled along with ancillary material handling equipment.
Figure 7:
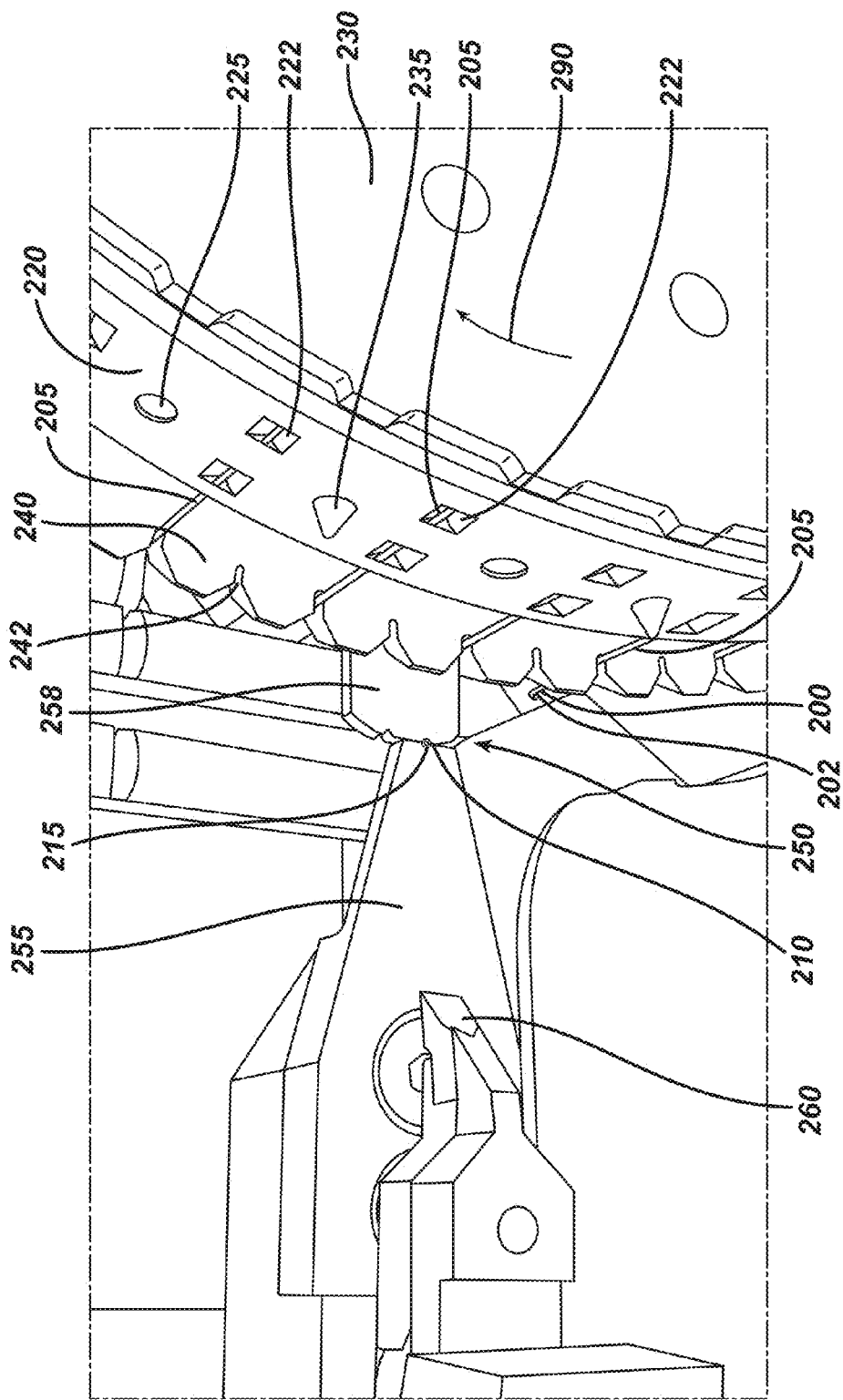
FIG. 7 is a side view of the fixture of FIG. 6 illustrating the needle being held in the jaws of the fixture.
Figure 8:
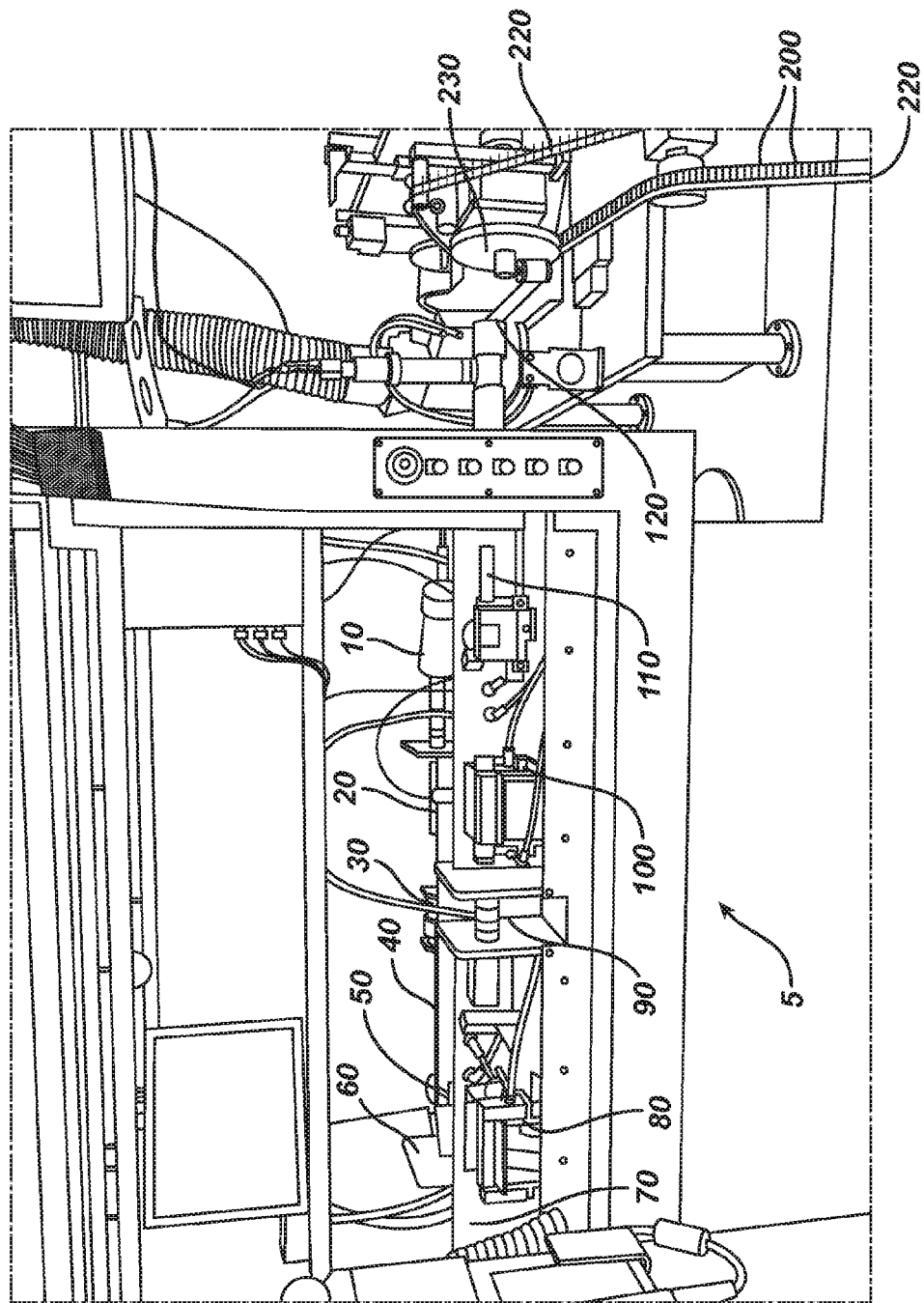
FIG. 8 is a photograph showing the laser drilling system of the present invention and the needle holding fixture.

Medical devices such as surgical needles are drilled using the novel laser drilling systems in the following manner. Referring to FIGS. 6, 7, and 8, a material handling system is partially illustrated wherein a surgical needle 200 is mounted in a conventional fixture 250. The needles 200 have proximal end 210, distal end 202 and tail section 205. The fixture 250 is seen to have clamping jaw member 255 and die 258 such that the proximal end 210 of the needle 200 is aligned with and adjacent to the beam focusing device 120 when contained between jaw member 255 and die 258. When the needle 200 is engaged in fixture 250, the tail end 205 is cut away from the needle 200 by cutting die 260 to expose the proximal end 210, simultaneously removing the needle 200 from carrier strip 220. The needles 200 are seen to be mounted to a conventional carrier strip 220 having pilot holes 225 driven by indexing drive wheel 230 having radially extending engagement pins 235 for engaging pilot holes 225. The needles are held onto the strip 220 by conventional tab members 222. The wheel 230 is seen to rotate in a clockwise manner in the direction of arrow 290. Mounted coaxially with the wheel 230 is the assist wheel 240 which has grooves 242 for engaging the tail sections 205 before and after they are cut away from the needle 200. The fixture 250 and focusing device 120 are adjusted and positioned such that laser beam 15 is preferably directed to impinge upon the center of the proximal end 210 of needle 200 to form drilled blind bore hole 215, although optionally the beam may be directed off-center to a degree as desired. The laser system 5 is adjusted and set up in the following manner. The seed laser 10 is adjusted to about 10-100% power, more preferably 100% power, the modulator device 30 is adjusted for a desired and efficiently effective number of pulses and pulse duration and frequency, and the solid state amplifiers 80 and 100 are adjusted for a desired and sufficiently effective voltage and current values and on-time durations to amplify the beam 15 before focusing on the needle. The amplifiers' power is defined by the voltage and current values and durations. It will be appreciated by those skilled in the art that the amplifiers will be selected based on the small signal gain and the saturation of amplification as known in the art. Small signal gain amplification is about 20-120×, more typically about 100×. These adjustments can be done manually through electronics panels for each device or they can be done through computer controlled programming. After each component is adjusted, a start switch is activated by the operator. This causes the needle handling unit to move each needle into position for drilling as described above. A servomotor sends a signal to a programmable logic controller (PLC) which in turn sends signal to a pulse delay generator to trigger each device in the laser system. The laser beam 15 is then emitted and contacts the proximal end 210 of each surgical needle 200 to drill a blind bore hole 215 having the required size and characteristics. Each drilled and cut needle 200 is removed from the carrier strip 220 after drilling, and the next undrilled needle 200 is indexed into place in fixture 250 for cutting and laser drilling of the bore holes 215.

Laser beam quality can be defined and measured as follows: when a pure Gaussian laser beam is focused, the width of the focused spot is defined by:

$$d_0 = 4\lambda f/\pi D_0$$

Where $d_0$ is the ideal focused spot width, $\lambda$ is the wavelength, f is the focal length of the lens, and $D_0$ is the width of the beam waist (diameter of the beam before it is focused). Subscript "0" refers to the idealized Gaussian beam.

However, when a distorted, or multimode beam is focused, the above equation becomes:

$$d = M^2 d_0$$

Where $M^2$ is a dimensionless parameter defining the quality of the beam, and where d is focused spot width for the real life beam. The real focused spot width is $M^2$ larger than expected for a pure Gaussian beam. The beam power density is thus $M^4$ times less than for a pure Gaussian beam.

The inventive system utilized in the following Examples used a seed fiber laser oscillator which had an $M^2=1.25$. For the whole inventive system, $M^2$ is estimated to be in the range of about 3 to about 6, although it will be appreciated that this value may vary depending upon the characteristics of the laser drilling system and individual components. The actual data on $M^2$ is contained in Example 3.

The following examples are illustrative of the principles and practice of the present invention, although not limited thereto.

Example 1

Boreholes Drilled in Surgical Needles Using the Laser Drilling System of the Present Invention Conventional stainless steel surgical needles having a wire size (diameter) of 0.66 mm (0.026") were drilled with a novel laser drilling system of the present invention as described herein. The novel laser system was able to drill holes of varying diameter and depth. The system parameters that were used are listed in Table 1.

TABLE 1

| Hole size | Number of Shots | Duty Cycle | Amplifier 1 Pulse | Amplifier 1 Voltage | Amplifier 2 Pulse | Amplifier 2 Voltage | Oscillator Pulse | Oscillator Power |
|---|---|---|---|---|---|---|---|---|
| 0.016" | 19 | 44% | 450 μs | 850 v | 300 μs | 880 v | 2 ms | 50 W |
| 0.012" | 17 | 44% | 400 μs | 750 v | 270 μs | 760 v | 2 ms | 50 w |
| 0.0052" | 23 | 35% | 450 μs | 485 v | 350 μs | 470 v | 2 ms | 50 w |

Figure 2A:
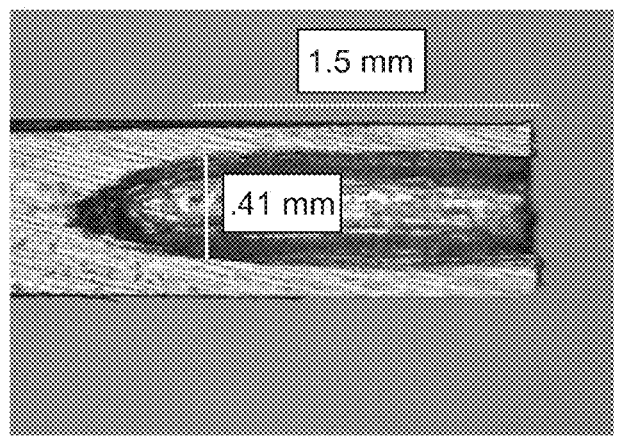
FIGS. 2A-C are photographs of cross-sections of the proximal ends of drilled surgical needles having bore holes drilled by a novel system of the present invention.
Figure 2B:
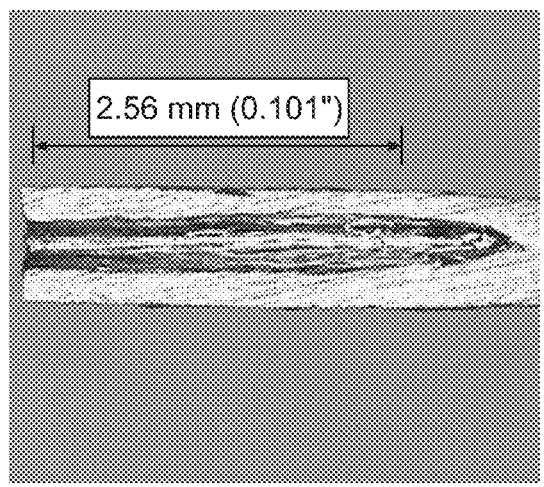
Figure 2C:
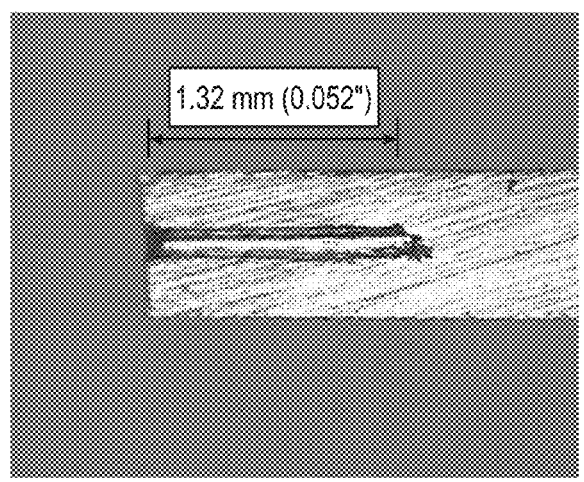
Figure 3A:
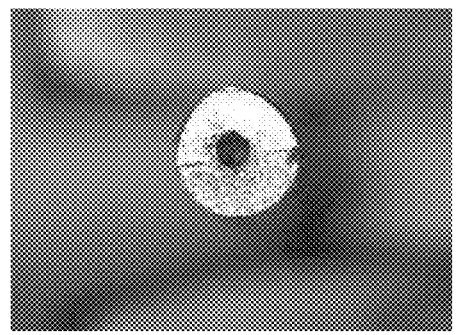
FIGS. 3A-C are photographs of the proximal end faces of the surgical needles of FIGS. 2A-C showing the bore holes having different diameters.
Figure 3B:
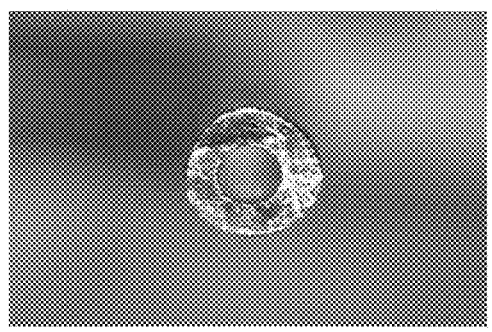
Figure 3C:
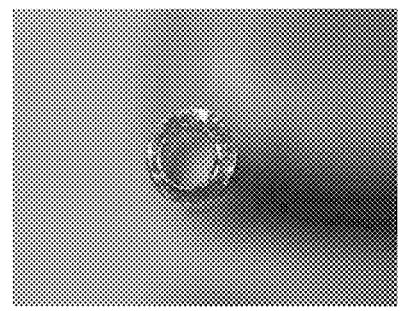

Photographs of cross-sections of the proximal ends of the needles having the drilled bore holes are seen in FIGS. 2A-C. Photographs of end views of the proximal ends of the needles showing the drilled bore holes are seen in FIGS. 3A-C. The bore holes can be described as very clean holes with no recast or remelt around the holes, having a depth from 1.32 mm (0.052") to 2.56 mm (0.101"). In addition, surprisingly, the system was capable of readily drilling the different bores holes (small, medium and large) having different diameters and depths.

Example 2

Comparison of Drilled Needles

Conventional stainless steel needles were drilled with a conventional flash lamp pumped laser drilling system and also with the novel laser drilling system of the present invention. The conventional system consisted of the following components: a flash lamp pumped solid state NdYag oscillator, a Pockels Cell and a flash lamp pumped solid state amplifier. When using the conventional flash lamp pumped laser system, the needles were drilled for comparison purposes both with and without the proximal suture mounting ends coated with blue ink. Identical surgical needles without ink coatings were drilled using the novel laser drilling system of the present invention. All of the needles had a needle wire size of 0.026 inches. The needles were made from Ethalloy™ stainless steel alloy. The needle parameters and laser parameters are contained in Table 2.

TABLE 2

| Flash Lamp Pumped System | NdYAG Seed Laser System |
|---|---|
| Needle Wire Size: 0.026 inches | 0.026 inches |
| Needle Alloy: Ethalloy ™ | Ethalloy ™ |
| Hole Diameter: 0.016 inches | 0.016 inches |
| Hole Depth: 0.055 inches | 0.055 inches |
| Laser Wavelength 1064 nm | 1064 nm |
| Oscillator Power: 2.8 KW | 50 W |
| Number of Modulated Pulses: 21 | 27 |
| Width of modulated pulses: 11 μs | 9.3 μs |
| Drilling Time: 0.5 ms | 0.5 ms |

Figure 4A:
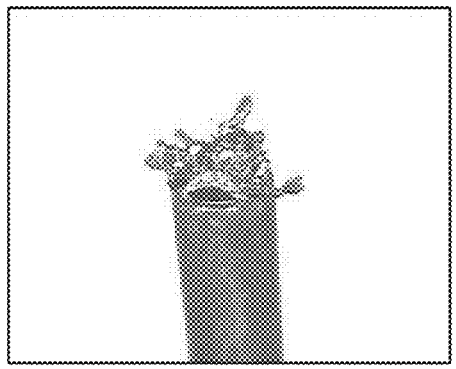
FIGS. 4A and 4B are photographs of the proximal ends of a conventional surgical needles having a bore hole drilled with a laser system of the prior art, wherein the ends of the needles were not coated with ink prior to drilling.
Figure 4B:
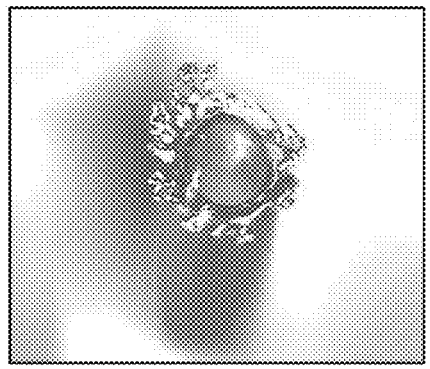
Figure 5:
FIG. 5 is a photograph of the proximal end of a conventional surgical needle having a bore hole drilled with a laser drilling system of the present invention, wherein the end of the needle was not coated with ink prior to drilling.

The needles drilled with the flash lamp pumped laser system as seen in the photographs in FIGS. 4A and 4B exhibited excessive recast and remelt when the needles were drilled without ink coatings. The needles drilled by the laser drilling system of the present invention which did not have ink coatings did not exhibit recast or remelt as illustrated by the photograph in FIG. 5.

Example 3

Comparison of Laser Beams for Beam Quality $M^2$ values for the conventional flash lamp pumped laser drilling system of Example 2 and the laser drilling system of the current invention (Example 1) having an NdYAG seed laser were measured using an Ophir-Spiricon $M^2$—200 s Beam Propagation Analyzer instrument. For the flash lamp pumped system of Example 2, the $M^2$ value measured to be 8, and, for the novel laser system of the present invention the $M^2$ value measured to be 2. This data showed that the laser system of the present invention had a laser beam quality that was 4 times better than the beam quality of the conventional laser system.

Although this invention has been shown and described with respect to detailed embodiments thereof, it will be understood by those skilled in the art that various changes in form and detail thereof may be made without departing from the spirit and scope of the claimed invention.

I claim:

1. A method of laser drilling bore holes in a surgical needle, comprising:

A. providing a percussive laser drilling system, comprising:
   a fiber seed laser producing a low power beam;
   a modulator to receive and pulse the beam;
   at least one solid state NdYAG amplifier to receive and amplify the pulsed beam, wherein the beam has a peak power of between about 5 kW to about 80 kW; and,
   focusing optics;
B. focusing the pulsed beam from the optics onto a proximal end of a surgical needle; and,
C. percussively drilling a bore hole in the proximal end of the surgical needle such that there is effectively no recast or remelt,
wherein the $M^2$ value of the focused and pulsed beam ranges from about 2 to about 6, and the focused and pulsed beam has a pulse duration of about 3 to about 30 microseconds.

2. The method of claim 1, wherein the drilling system additionally comprises a second amplifier.

3. The method of claim 1, wherein the laser system has an average beam power of about 0.5 to about 80 watts.

4. The method of claim 1, wherein the amplifier is flash lamp pumped.

5. The method of claim 2, wherein the second amplifier is flash lamp pumped.

6. The method of claim 1, wherein the amplifier is diode pumped.

7. The method of claim 2, wherein the second amplifier is diode pumped.

8. The method of claim 1, additionally comprising a processor to control the system and the beam.

9. The method of claim 1, wherein the bore hole is a blind bore hole.

10. The method of claim 1, wherein the fiber seed laser is a Ytterbium fiber seed laser.

* * * * *